(12) United States Patent
Kullenberg et al.

(10) Patent No.: US 9,588,065 B2
(45) Date of Patent: Mar. 7, 2017

(54) METHOD AND APPARATUS FOR MEASUREMENT OF CONCENTRATION OF A SPECIFIC ANALYTE IN A BIOLOGICAL MATERIAL

(71) Applicant: MANTEX AB, Kista (SE)

(72) Inventors: Ragnar Kullenberg, Oskarström (SE); Ralf Torgrip, Älvsjö (SE); Fredrik Danielsson, Västerås (SE); Eric Landström, Stockholm (SE)

(73) Assignee: Mantex AB, Kista (SE)

( * ) Notice: Subject to any disclaimer, the term of this patent is extended or adjusted under 35 U.S.C. 154(b) by 260 days.

(21) Appl. No.: 14/538,159

(22) PCT Filed: Jun. 12, 2013

(86) PCT No.: PCT/EP2013/062111
§ 371 (c)(1),
(2) Date: Nov. 12, 2014

(87) PCT Pub. No.: WO2013/189795
PCT Pub. Date: Dec. 27, 2013

(65) Prior Publication Data
US 2015/0323475 A1  Nov. 12, 2015

(30) Foreign Application Priority Data
Jun. 19, 2012 (EP) .................... 12172578

(51) Int. Cl.
*G01N 23/06* (2006.01)
*G01N 23/08* (2006.01)
(Continued)

(52) U.S. Cl.
CPC ......... *G01N 23/10* (2013.01); *G01N 21/0303* (2013.01); *G01N 21/5911* (2013.01);
(Continued)

(58) Field of Classification Search
CPC ...... G01N 23/06; G01N 23/08; G01N 23/083; G01N 23/087; G01N 23/10
(Continued)

(56) References Cited

U.S. PATENT DOCUMENTS 3,711,707 A * 1/1973 Lilienfeld .............. G01N 23/08
250/308
5,146,413 A * 9/1992 Shires .................... G01F 17/00
702/25
(Continued)

FOREIGN PATENT DOCUMENTS

EP 0634642 1/1995
FR 804984 11/1936
(Continued)

OTHER PUBLICATIONS

Sarah A. Stewart et al., "Variable Path-Length Cells for Discovery-Babsed Investigation of the Beer-Lambert Law", Journal of Chemical Eduction, vol. 76, No. 3, Mar. 1, 1999, pp. 399-400, XP055044551, ISSN: 0021-9584.
(Continued)

*Primary Examiner* — Allen C. Ho
(74) *Attorney, Agent, or Firm* — Babcock IP, PLLC

(57) ABSTRACT

A method and apparatus for determining the concentration of a specific analyte in a sample of biological material are disclosed. The sample is placed in a sample container (10) which provides at least two radiation paths (14) with different lengths through the sample container (10), and is sequentially irradiated with electromagnetic radiation, e.g. X-rays. The amount of radiation penetrating the sample is detected, and absorbance is determined based on the detected radiation. During irradiation, the sample container (10) is moved in relation to the radiation source (1) and detector (5) so that absorbance measurements at different path-lengths are acquired. A regression line from the absor-
(Continued)

bance values and path lengths is determined, such that a slope of the regression line is obtained, and based on this slope, the concentration of the specific analyte is determined.

19 Claims, 1 Drawing Sheet

(51) Int. Cl.
    *G01N 23/083*     (2006.01)
    *G01N 23/087*     (2006.01)
    *G01N 23/10*     (2006.01)
    *G01N 21/03*     (2006.01)
    *G01N 21/59*     (2006.01)

(52) U.S. Cl.
    CPC .............. *G01N 23/06* (2013.01); *G01N 23/08* (2013.01); *G01N 23/083* (2013.01); *G01N 23/087* (2013.01); *G01N 2223/32* (2013.01); *G01N 2223/619* (2013.01)

(58) Field of Classification Search
    USPC .................................................. 378/53, 208
    See application file for complete search history.

(56) References Cited

U.S. PATENT DOCUMENTS

| | | | | |
|---|---|---|---|---|
| 6,147,351 A * | 11/2000 | Huiku | ................ | G01N 21/0303 250/343 |
| 6,249,345 B1 * | 6/2001 | Kraack | .............. | G01N 21/0303 356/244 |
| 6,342,948 B1 * | 1/2002 | Gilby | ................. | G01N 21/0303 356/246 |
| 7,808,641 B2 * | 10/2010 | Salerno | .............. | G01N 21/0303 356/440 |
| 8,515,008 B2 * | 8/2013 | Ullberg | ................ | G01N 23/223 250/360.1 |
| 9,404,851 B2 * | 8/2016 | Shih | ....................... | G01N 21/31 |
| 2010/0098211 A1 | 4/2010 | Hill | | |

FOREIGN PATENT DOCUMENTS

| | | |
|---|---|---|
| WO | WO0031512 | 6/2000 |
| WO | WO2007126389 | 11/2007 |
| WO | WO2008132611 | 11/2008 |

OTHER PUBLICATIONS

James Gordon et al, "A Graduation Cylinder Colorimeter: An Investigation of Path Length and the Beer-Lambert Law", Journal of Chemical Education, vol. 79, No. 5, May 1, 2002, p. 911, XP055044560, ISSN: 0021-9584.

Emma Dedman, International Search Report for PCT/EP2013/062111, Jul. 8, 2013, Rijswijk Netherlands.

\* cited by examiner

METHOD AND APPARATUS FOR MEASUREMENT OF CONCENTRATION OF A SPECIFIC ANALYTE IN A BIOLOGICAL MATERIAL

TECHNICAL FIELD OF THE INVENTION

The present invention relates to a method and an apparatus for determining the concentration of a specific analyte in a sample of biological material.

BACKGROUND

Spectroscopic or spectrometric analysis is a broad field in which the composition and properties of an analyte in any phase, viz, gas, liquid, solid, are determined from the residual electromagnetic spectra arising from the interaction (eg. absorption, luminescence, or emission) of the analyte and energy. One aspect of chemical analysis, known as absorptiometry, involves interaction of radiant energy with the analyte of interest. One such method is known as absorption photometry, in which the optical absorption of samples are measured. The absorption is the amount of energy absorbed by the sample. In a simple spectrophotometer the studied sample material is placed in a container, also known as a cuvette or sample cell. Electromagnetic radiation (light) of a known wavelength, $\lambda$, (i.e. ultraviolet, infrared, visible, etc.) and intensity $I_0$ is incident on one side of the cuvette. A detector, which measures the intensity of the transmitted light, I is placed on the opposite side of the cuvette. The length that the light propagates through the sample is the distance d. Most standard UV/visible spectrophotometers utilize standard cuvettes which have up to 1 cm path lengths, and often much shorter, and normally hold 50 to 2000 µL of liquid sample. For a sample consisting of a single homogeneous substance with a concentration c, the light transmitted through the sample will follow a relationship know as the Beer-Lambert Law: $A=\epsilon cd$ where A is the absorbance (also known as the optical density (OD) of the sample at wavelength $\lambda$, where OD=the $-\log$ of the ratio of transmitted light to the incident light), $\epsilon$, is the absorptivity or extinction coefficient (normally at constant at a given wavelength), c is the concentration of the sample and d is the path length of radiation through the sample. In most spectrophotometers the path length, d, is fixed.

It is known that usually the $\epsilon$ is high resulting in that cuvettes with small d must be used in order to record any transmission. It is also known that it is possible to alter the path length, d, for measurement of highly concentrated samples. This is used to provide a possibility of choosing an appropriate path length for different measurements, and for the measurement, a single path length and single wavelength measurements are used. Such systems are e.g. known from WO 2007/126389, U.S. Pat. No. 6,249,345 and DE 85 33 381.

It is also known that it is possible to use a variable path length during one measurement, and to use a regression line analysis of the resulting path-length dependent attenuations to determine the concentration of a sample. This is shown in U.S. Pat. No. 7,808,641, and is referred to as slope spectroscopy. However, slope spectroscopy requires a moveable probe which is inserted into the sample material, and which is adjusted to different pathlengths. The complex set-up and interaction with the sample material to be measured makes this method cumbersome and expensive, and also provides limited practical use since the described method can only be used for certain types of liquid solutions. Further, it is also difficult to obtain adequate calibration.

There is therefore a need for a faster and simpler method and apparatus for estimating the concentration of an analyte in a sample material, and in particular a solid material, such as in wood, which alleviates the above-discussed drawbacks of the prior art.

SUMMARY OF THE INVENTION

It is therefore an object of the present invention to provide an improved method and apparatus for measuring the concentration of a specific analyte in a sample of a biological material, which overcome or at least alleviate the above-discussed problems of the prior art.

This object is achieved by means of the invention as defined in the appended claims.

According to a first aspect of the invention there is provided a method of determining the concentration of a specific analyte in a sample of biological material, the method comprising:

placing the sample of biological material in a sample container, wherein the geometry of the sample container provides at least two irradiation paths with different lengths through the sample container;

sequentially irradiating the sample with electromagnetic radiation emitted by an irradiation source arranged at one side of the sample container through said at least two paths;

detecting the amount of radiation transmitted through said sample using a detector arranged on an opposite side of said sample container;

determining the absorbance based on said detected radiation;

wherein during said steps of sequential irradiation, the sample container is moved in relation to the irradiation source and detector, whereby the electromagnetic radiation passes through at least said two paths of different lengths, such that an absorbance reading is determined at a predetermined wavelength at said different path lengths;

generating a regression line using the absorbance values and path lengths such that a slope of the regression line is obtained; and determining the concentration of the specific analyte by dividing the slope of the regression line by the extinction coefficient of the analyte.

The term "moving the sample container in relation to the irradiation source and detector" or "moving the sample container" means that the sample container is moved relative to the radiation source. This encompasses the situations where the sample container is moving and the radiation source and detector are stationary, the radiation source and detector are moving and the sample container is stationary and where both the sample container and the radiation source and detector are moving.

The term "determining the absorbance" means that any absorbance reading(s) is measured by the device or instrument. This encompasses situations where the absorbance reading is taken at a single wavelength and/or a single path length or where the reading is taken at multiple wavelengths (such as in a scan) and/or multiple path lengths.

The present invention is based on the understanding that the Beer-Lambert law may be used to determine the concentration of a specific analyte. The Beer-Lambert law states that $A=\log(I/I_0)=\epsilon cd$ where A is the absorbance of the sample at a certain wavelength, $\epsilon$, is the absorptivity or extinction coefficient, c is the concentration of the sample and d is the path length of radiation/energy through the sample. From this follows that A*1/εc=d, which means that A is proportional to d, and plotting of A against d forms a linear regression line with a slope 1/εc. The present invention provides a very efficient and robust way of determining pairs of A and d values, enabling a reliable and robust measurement of the concentration c.

By measuring the transmitted radiation through the sample, wherein the radiation source is arranged at one side of the sample container and the detector is arranged on an opposite side, neither the radiation source nor the detector need to be in contact with the sample material. The radiation source and the detector can here be arranged close to the sample container, or even in contact with the sample container, or at a certain distance from the sample container. This provides a significantly simplified and more cost-efficient set-up. Further, this makes it possible to measure on a much wider range of analytes. For example, there is now no need for the material to be in liquid form, and measurements can e.g. be made directly on solid materials. This also makes the invention particularly useful for measurements on biological materials. For example, it is hereby possible to measure the concentration of specific analytes in wood chips, but it may also be used for other forms of wood, as well as for other types of biological material, such as pulp, biomass fuel, crop, such as corn, grain and sugar cane, etc. The invention is particularly useful for biological material in a liquid or separated form, and preferably in the form of chips.

The present invention also leads to simplified sample preparation, and to a faster and more cost-efficient analysis.

Further, the present invention enables a simplified and more reliable calibration, which in turn makes the method more robust, and provides more reliable measurement results. By means of the present invention, calibration can be made independent on the path length, d. This is e.g. a particular advantage when the sample material in itself is inhomogeneous on a macro level, i.e. when the sample material has formation sizes comparable to or larger than the wavelength of the radiation used for measurement.

The present invention provides an interactive variable path length apparatus and method for spectroscopic measurement of a sample. The instruments of the present invention can be used to measure the concentration of very concentrated samples, or less concentrated samples. Furthermore, the instruments and methods of the present invention can provide spectrum scans in two or three different path length zones. This enables users to determine optimal absorbance peaks in a sample in a single run. Hereby, it can provide information on optimization of concentration measurements by comparing absorbance peak data at multiple path lengths and multiple wavelengths as these values can be different due to the contents in the sample.

The apparatus and methods of the present invention can be used in conjunction with a standard spectrophotometer which may be used to provide an electromagnetic source and/or a detector for measuring electromagnetic radiation.

The sample container preferably comprises a circumferential wall having a radiation incident wall portion and a radiation emerging wall portion, the radiation emerging wall portion being opposite to said radiation incident wall portion, wherein said sample compartment is designed such that it has at least two different optical path lengths between the radiation incident wall portion and the radiation emerging wall portion.

According to one line of embodiments, the sample container is designed such that it has a plurality of discrete optical path lengths between the radiation light incident wall portion and the radiation emerging wall portion. Hereby, there is a stepwise transition between parts of the sample container having different paths lengths, and by moving the sample container, the radiation occurs through said discrete path lengths sequentially. In this line of embodiments, the sample container may e.g. have a least one of the wall portions being arranged as a stepped wall. The corresponding, opposite wall may be planar. However, alternatively, both the walls may have a stepwise configuration, providing the shape of a step wise narrowing wedge.

Alternatively or additionally, the sample container may be designed such that it has a continuously changing optical path length between at least a section of the radiation incident wall portion and a corresponding section of the radiation emerging wall portion along the height and/or width of the sample container. Hereby, a continuous transition between different path lengths may be obtained during measurement, while moving the sample container in a length or width direction, respectively. The sample container may here have one planar, vertical, wall, and an opposite wall also being planar, but arranged obliquely, with an angle relative to the first wall. Alternatively, the oblique wall may be arranged in two or more different angles relative to the first wall. Further, both walls may be oblique. Thus, the sample container may take the form of a wedge, tapering in the direction towards one end. The sample container may also take the form of a prism with triangular cross-section. The triangular cross-section may be a right-angled triangle, an equilateral triangle, or have other angular configurations.

The tapering form of the sample container may e.g. be in the form of a wedge, a cone or a frusto-conical cone. Thus, the length of the irradiation path may be varied by moving the radiation beam, which may typically be perpendicular to the tapering direction, in the tapering direction.

According to a preferred embodiment, the sample container is arranged to provide at least five different irradiation paths through the sample during irradiation, said irradiation paths all being of different lengths through said sample. Even more preferably the apparatus may be arranged to scan the irradiation beam through a part of the sample container, thereby provide a multitude of varying irradiation paths through said mineral sample during irradiation.

The step of determining the concentration of the analyte is preferably based on deriving the slope of a line based on the ratio of path length to absorbance values.

The electromagnetic radiation is preferably in the X-ray range. The use of X-ray radiation provides many advantages. Since it penetrates through most materials, it makes it possible to measure on essentially any material. Further, since the penetration depth for X-ray energy is very large compared to e.g. visible light and infra red (IR), it makes it possible to use much larger sample containers, which enables the analysis of relatively large samples and minimizes the tedious work of sample preparation etc. Further, it makes it possible to measure over greatly differing pathlengths, which makes the measurement very robust.

The amount of radiation transmitted through the sample of the material is preferably determined in relation to a calibration reference sample of the material of known composition. The calibration reference value may be determined by measurement of the transmission of radiation through a reference material, said calibration measurement preferably being made immediately before and/or after the measurement through the sample material.

According to another aspect of the present invention, there is provided an apparatus for determining the concentration of a specific analyte in a sample of biological material comprising:

a sample container that can contain the sample material, and the geometry of which provides at least two irradiation paths with different lengths through the sample container;

a radiation source arranged at one side of the sample container for generating an electromagnetic irradiation;

a detector located opposite to the radiation source, and on a different side of the sample container, so that the detector can detect electromagnetic radiation being transmitted through said sample container along said at least two paths; and, a motor operably linked to the sample container such that the sample container can be moved relative to the radiation source to provide variable path lengths;

a controller having software for calculating the concentration of the sample based on the information provided by the detector at the predetermined path lengths; generating a regression line from the absorbance and path length such that a slope of the regression line is obtained; and determining the concentration of the specific analyte by dividing the slope of the regression line by the extinction coefficient of the sample.

The term "motor" is any device that can be controlled to provide a variable path length through a sample.

Hereby, similar advantages and preferred embodiments as discussed above in relation to the first aspect are achievable.

The sample container preferably comprises a circumferential wall having a radiation incident wall portion and a radiation emerging wall portion, the radiation emerging wall portion being opposite to said radiation incident wall portion, wherein said sample compartment is designed such that it has at least two different optical path lengths between the radiation incident wall portion and the radiation emerging wall portion.

The sample container may be designed such that it has a plurality of discrete optical path lengths between the radiation incident wall portion and the radiation emerging wall portion. Preferably, at least one of said wall portions is a stepped wall.

Additionally or alternatively, the sample compartment may be designed such that it has a continuously changing optical path length between at least a section of the radiation incident wall portion and a corresponding section of the radiation emerging wall portion along the height and/or width of the sample container.

In a preferred embodiment, the sample container has a tapered form.

The software run by the controller is preferably arranged to calculate the concentration based on deriving the slope of a line based on the ratio of path length to absorbance values.

The sample container is preferably arranged to be continuously moved along a predetermined path in such a manner that in the course of the measurement the radiation beam passes through at least said two different radiation paths. In one embodiment, the sample container may be rotatably arranged, and preferably being rotatable during said irradiation. However, preferably the sample container is linearly moveable, and preferably in a direction corresponding to a longitudinal direction of said sample container. Alternatively, the sample container may be linearly moved in a direction corresponding to a width direction of the sample container.

The electromagnetic radiation is preferably within the X-ray range, whereby the radiation source is an X-ray source.

The apparatus may further comprise controller means to adjust an X-ray tube voltage of said X-ray source in accordance with the length of the irradiation paths.

The X-ray source is preferably operated in the energy range 20-150 kVp, and preferably 40 kVp-160 kVp. Here, kVp (Peak kilovoltage) denotes the maximum voltage applied across an X-ray tube. It determines the kinetic energy of the electrons accelerated in the X-ray tube and the peak energy of the X-ray emission spectrum. The actual voltage across the tube may fluctuate.

The length of the longest of the irradiation paths through said sample is preferably at least 50 mm, and more preferably at least 80 mm, and most preferably at least 100 mm. The use of such a large sample container enables the method to be used on e.g. biological materials having relatively large structural features, and also makes the measurement very robust. The length of the irradiation paths through the sample are preferably relatively evenly distributed between the shortest irradiation path, which may e.g. be close to 0, or only a few mm, and said longest irradiation path, so that it varies between essentially said end values.

Preferably, the length difference between the shortest path and the longest path of the at least two paths used for the measurement is at least 20 mm, and even more preferred at least 30 mm, and most preferably at least 50 mm. This enables a very robust and reliable measurement.

While the preferred embodiments of the methods and apparatus of the present invention are intended to determining the absorbance, extinction coefficient or concentration of an analyte in a particular sample or set of samples, the apparatus and method of the present invention may additionally also be used in different modes such as scattering, as well as other modalities. The devices and the methods of the present invention may be used to determine optical values of one or more samples at a given time.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein.

DETAILED DESCRIPTION OF PREFERRED EMBODIMENTS

Figure 1:
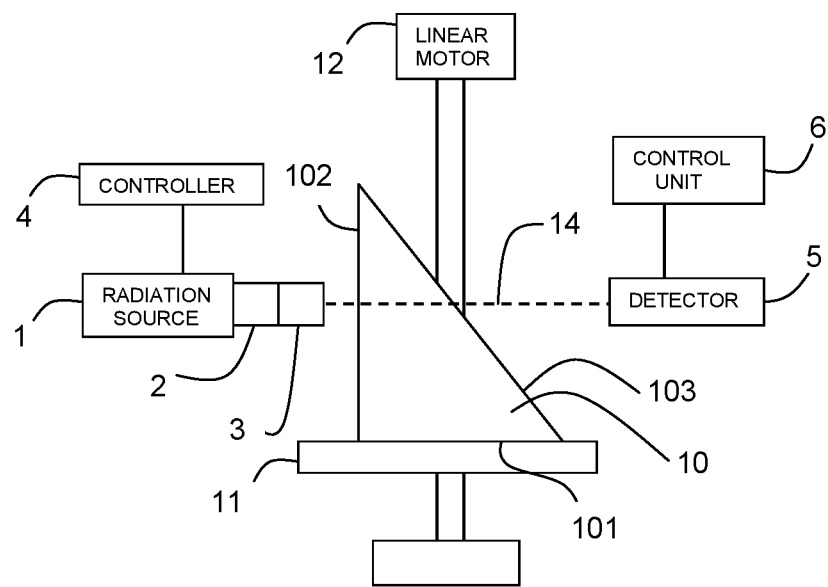
FIG. 1 is a schematic side view of a measurement apparatus according to an embodiment of the present invention.

Referring to FIG. 1, an exemplary measurement apparatus according to the present invention comprises a radiation source 1 for providing radiation of one or several energy level(s)/wavelength(s). Preferably, the radiation source is an X-ray tube for provision of X-ray radiation of two or more different wavelengths. Preferably, the X-ray tube operates in the range 20-150 kVp. The output radiation from the radiation source 1 is preferably directed towards a target area through a collimator 2 and a lens 3. The radiation source 1 is controlled by means of a controller 4.

On the opposite side of the target area, a detector 5 is arranged to receive radiation transmitted through material arranged in the target area. The detector 5 comprises any mechanism capable of converting energy from detected radiation into signals that may be processed by the apparatus. The detector 5 is preferably a semiconductor detector, comprising an array of semiconductor detector areas. Detector(s) is/are used to measure absorbance, but in addition, detector(s) may be used to measure photoluminescence and scattering. The apparatus may comprise one or several detectors. The detector 5 is connected to a control unit 6 with a processor, e.g. an ordinary personal computer. The control unit 6 receives signals from the detector 5 through a suitable interface, such as through a USB port.

The controller 4 controlling the radiation source 1 may also be connected to the control unit 6, or be formed as an integrated part of the control unit 6.

The material to be measured is arranged in a sample container 10. The sample container 10 is arranged on a carrier 11, which is movable in such a way that the sample container 10 is moved through the target area, and through the radiation path 14. The carrier 11 may e.g. be moved by means of a linear motor 12. However, other means for moving the carrier 11 are also feasible, such as conveyors, screw arrangements, rail arrangements and the like. The motor 12 can e.g. be a stepper motor, servo, piezo, electric and magnetic motors or any device that can be controlled to provide a variable path length through a sample. The carrier 11 may be supported by a stage. The motor 12 drives the carrier 11 in precise steps to vary the path length through the sample, or continuously.

As will be discussed in more detail in the following, the sample container 10 provides at least two irradiation paths with different lengths through the sample container 10. The radiation source 1 is arranged on one side of the sample container 10, and the detector 5 is located opposite the radiation source 1, on the opposite side of the sample container 10. Hereby, the detector 5 can detect electromagnetic radiation being transferred through the sample container 10, and with the sample container 10 being moved, it is possible to measure at at least two path-lengths.

The control unit 6 is further provided with a software for calculating the concentration of a specific analyte in the sample based on the information provided by the detector 5 at the predetermined path lengths. To this end, the software generates a regression line from the absorbance and path length such that a slope of the regression line is obtained, and determines the concentration of the specific analyte by dividing the slope of the regression line by the extinction coefficient of the sample. Such software is per se previously known, and is disclosed in U.S. Pat. No. 7,808,641, said patent hereby being incorporated by reference in its entirety.

The control software will preferably adapt the apparatus behavior based upon various criteria such as but not limited to wavelength, path length, data acquisition modes (for both wavelength/path length), kinetics, triggers/targets, discrete path length/wavelength bands to provide different dynamic ranges/resolutions for different areas of the spectrum, cross sectional plot to create abs/path length curves, regression algorithms and slope determination, concentration determination from slope values, extinction coefficient determination, base line correction, and scatter correction. The software is preferably configured to provide scanning or discrete wavelength read options, signal averaging times, wavelength interval, scanning or discrete path length read options, data processing option such as base line correction, scatter correction, real-time wavelength cross-section, threshold options (such as wavelength, path length, absorbance, slope, intercept, coefficient of determination, etc.) an kinetic/continuous measurement options.

The multiple absorbance measurements made at different path lengths enables an accurate calculation of the concentration, by calculation of a regression line from the absorbance and path length information. The slope of the regression line can then be used to calculate the concentration of the sample. Each path length need not be accurately known due to the fact that the software used to calculate the regression line can be programmed to select the most accurate line from the data set presented.

Hereby, calculation of concentration is based on calculation of the extinction coefficient of a particular sample at one or several different wavelengths. The extinction coefficient, also known as absorptivity, is the absorbance of a solution per unit path length and concentration at a given wavelength. If the extinction coefficient for a given sample is known at a first wavelength one can calculate the extinction coefficient at a second wavelength. This is done by measuring the ratio of the absorbance/path length at the first wavelength to the absorbance/path length at a second wavelength and equating this ratio to the ratios of the extinction coefficients. It is also possible to measure the components in a complex mixture/sample at the same time as long as the wavelengths that identify the multiple components in the sample can be separated. For example, it is hereby possible to determine the concentration of a specific sample analyte, where there are two or more materials present in the sample material. This is possible since the path length can be altered so that the concentration of the different components can be determined together. Obviously, as long as there are peaks which uniquely identify a component within a sample the methods of the present invention can measure the concentration of the components of very complex samples. Additionally because the instrument is capable of generating data in real-time, the interaction of components within the sample can be monitored to produce kinetic data or any data for which a time course is required.

Thus, for measurement, the sample container 10 is moved in relation to the radiation source 1 and detector 5, in order to sequentially irradiating the sample with electromagnetic radiation emitted by the radiation source 1 through the at least two paths in the sample container 10. The sequential measurement may be a continuous measurement performed during a continuous movement of the sample container 10 or an intermittent measurement while the sample container 10 is continuously moved. Alternatively, the sample container 10 may also be moved in discrete steps.

Hereby, measurement at variable path lengths is made very efficient. The values of the absorbance at various path lengths can then be used to calculate the concentration of a compound in the solution. Further, the broad dynamic range being provided enables users to determine the concentrations of their samples without altering (diluting or concentrating) the samples by selecting appropriate path-lengths of the scan.

The sample container 10 may be configured and shaped in various ways, as would be apparent for the skilled reader. In the embodiment of FIG. 1, the sample container 10 is shaped as a prism, with a right-angled triangular cross-section. Hereby, the sample container 10 has a horizontal base plane 101, a vertical first side plane 102, being arranged closest to the radiation source 1, and thereby functioning as the radiation incident wall, and an obliquely arranged second side plane 103, being arranged closest to the detector 5, and thereby functioning as a radiation emerging wall. This configuration provides a multitude of different path lengths through the material, extending to very short path lengths at the top and very long path lengths at the bottom. The path length may change gradually along any section of one of the wall portions. It may change in any selected direction, for instance along the height and/or the width of the sample container 10. The path length may change continuously along the entire height and/or along the entire width of the sample container 10, or over only a part of the height and/or width.

Figure 2A:
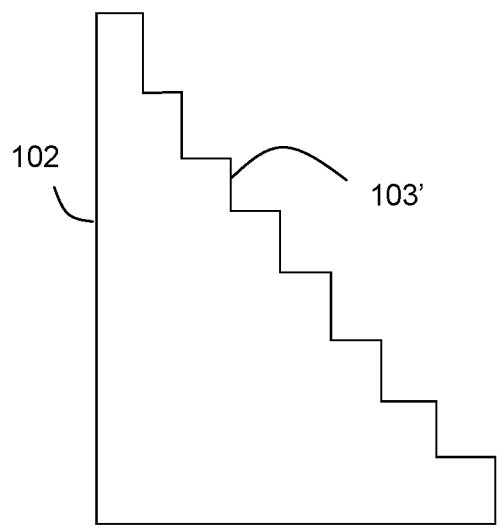
FIG. 2 are simplified side views of alternative sample containers.

In an alternative sample configuration, illustrated in FIG. 2A, the oblique second side plane 103 is replaced with a stepped wall 103', providing several horizontal wall parts, each being arranged at different distances from the first side plane 102. Hereby, a sample container 10 providing a plurality of discrete optical path lengths is obtained. As a further alternative, both wall portions may have multiple perpendicular steps.

Figure 2B:
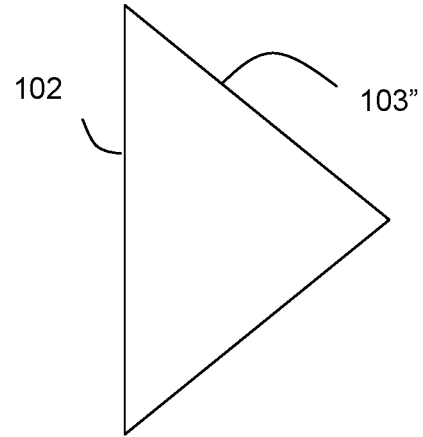

Yet another alternative sample configuration is illustrated in FIG. 2B. Here, the oblique second side plane 103" comprises first and second sections, being arranged with an angle in relation to each other, so that the path lengths continuously increases from the top and downward, to the intersection between the first and second sections, and thereafter again decreases. In this configuration, the sample container 10 is provided with a cross-section resembling an equilateral triangle.

The sample container 10, or at least the side walls through which radiation is to enter or emerge, is made of a material which allows the electromagnetic radiation used to pass through it. The sample container 10 also comprises an opening, e.g. arranged on a side wall parallel to the radiation path, to allow samples to be entered to or removed from the sample container 10.

A calibration step is preferably used prior to, during or after the measurement, whereby the amount of radiation transmitted through the reference sample of the material of known composition is determined.

In the foregoing, the set-up has been disclosed as being oriented such that the radiation source 1 is on one side and the detector 5 on the other side, and the sample container 10 is moved vertically upwards or downwards. However, other orientations are possible, and e.g. the sample container 10 may be moved in a horizontal direction instead. Further, the radiation need not penetrate the sample container 10 in a vertical direction, but oblique directions are also feasible. Regardless of the absolute spatial orientation of the radiation source 1 and the detector 5, the radiation source 1 and the detector 5 are preferably arranged along a single line.

Specific embodiments of the invention have now been described. However, several alternatives are possible, as would be apparent for someone skilled in the art. For example, the radiation need not be X-ray, but other types of electromagnetic radiation may also be used. Further, the sample container 10 may have various shapes and configurations. Further, the relative movement between the sample container 10 and radiation beam(s) may be provided in various ways. Still further, the implementation of the control and processing method could be accomplished in different ways, such as in especially dedicated hardware or in software for control of already existing control means.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

We claim:

1. A method of determining a concentration of a specific analyte in a sample of biological material, the method comprising:
   placing the sample of biological material in a sample container, wherein a geometry of the sample container provides at least two irradiation paths with different path lengths through the sample container;
   sequentially irradiating the sample with electromagnetic radiation emitted by a radiation source arranged at one side of the sample container through said at least two irradiation paths;
   detecting an amount of electromagnetic radiation transmitted through said sample using a detector arranged at an opposite side of the sample container;
   determining an absorbance value based on said detected electromagnetic radiation;
   wherein the step of sequentially irradiating comprises moving the sample container in relation to the radiation source and the detector, whereby the electromagnetic radiation passes through said at least two irradiation paths of different path lengths,
   determining an absorbance reading at a predetermined wavelength at said different path lengths;
   generating a regression line using the absorbance values and the different path lengths,
   obtaining a slope of the regression line; and
   determining the concentration of the specific analyte by dividing the slope of the regression line by an extinction coefficient of the specific analyte.

2. The method of claim 1, wherein the sample container comprises a plurality of discrete optical path lengths between a radiation incident wall portion and a radiation emerging wall portion.

3. The method of claim 1, wherein said sample container comprises a continuously changing optical path length between at least a section of a radiation incident wall portion and a corresponding section of a radiation emerging wall portion along a height and/or a width of the sample container.

4. The method of claim 1, further comprising determining an amount of electromagnetic radiation transmitted through the sample of the biological material in relation to a calibration reference sample of known composition.

5. The method of claim 4, further comprising determining a calibration reference value by measurement of the transmission of electromagnetic radiation through the calibration reference sample material of known composition.

6. The method of claim 1, wherein said sequentially irradiating the sample with electromagnetic radiation comprises irradiating the sample with electromagnetic radiation in the X-ray range, emitted by an X-ray source arranged at one side of the sample container, through said at least two irradiation paths.

7. An apparatus for determining a concentration of a specific analyte in a sample of biological material comprising:

a sample container that can contain a sample, and a geometry of which provides at least two irradiation paths with different path lengths through the sample container;

a radiation source arranged at one side of the sample container for generating an electromagnetic radiation;

a detector located opposite to the radiation source, and on a different side of the sample container, so that the detector can detect electromagnetic radiation being transmitted through said sample container along said at least two irradiation paths; and a motor configured to move the sample container relative to the radiation source to provide variable path lengths;

a controller having software configured to:
  calculate a concentration of the sample based on the information provided by the detector at different path lengths;
  generate a regression line from an absorbance and a path length to obtain a slope of the regression line; and
  determine a concentration of a specific analyte by dividing the slope of the regression line by an extinction coefficient of the sample.

8. The apparatus of claim 7, wherein the sample container comprises a circumferential wall having a radiation incident wall portion and a radiation emerging wall portion, the radiation emerging wall portion being opposite to said radiation incident wall portion, wherein said sample container comprises at least two different optical path lengths between the radiation incident wall portion and the radiation emerging wall portion.

9. The apparatus of claim 8, wherein the sample container comprises a plurality of discrete optical path lengths between the radiation incident wall portion and the radiation emerging wall portion, and wherein at least one of said wall portions comprises a stepped wall.

10. The apparatus of claim 8, wherein said sample container comprises a continuously changing optical path length between at least a section of the radiation incident wall portion and a corresponding section of the radiation emerging wall portion along a height and/or a width of the sample container.

11. The apparatus of claim 8, further comprising a carrier configured to continuously move the sample container along a predetermined path in such a manner that in the course of a measurement the electromagnetic radiation passes through said at least two different irradiation paths.

12. The apparatus of claim 11, wherein the carrier is configured to move the sample container linearly.

13. The apparatus of claim 11, wherein the electromagnetic radiation comprises an X-ray range, and said radiation source comprises an X-ray source.

14. The apparatus of claim 8, wherein the electromagnetic radiation comprises an X-ray range, and said radiation source comprises an X-ray source.

15. The apparatus of claim 7, wherein the electromagnetic radiation comprises an X-ray range, and said radiation source comprises an X-ray source.

16. The apparatus of claim 15, further comprising a controller to adjust an X-ray tube voltage of said X-ray source in accordance with the different path lengths of the at least two irradiation paths.

17. The apparatus of claim 7, wherein the length of the longest of the at least two irradiation paths through said sample is at least 50 mm.

18. The apparatus of claim 17, wherein the path length difference between the shortest irradiation path and the longest irradiation path of the at least two irradiation paths used for the measurement is at least 20 mm.

19. The apparatus of claim 7, wherein the path length difference between the shortest irradiation path and the longest irradiation path of the at least two irradiation paths used for the measurement is at least 20 mm.

* * * * *